(12) United States Patent
Meiners

(10) Patent No.: US 8,740,990 B2
(45) Date of Patent: Jun. 3, 2014

(54) RANDOMLY ORIENTED, FGF-2-MODIFIED NANOFIBER DEVICE FOR USE IN SPINAL CORD REPAIR

(75) Inventor: Sally Meiners, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1322 days.

(21) Appl. No.: 12/519,542

(22) PCT Filed: Dec. 21, 2007

(86) PCT No.: PCT/US2007/088493
§ 371 (c)(1),
(2), (4) Date: Sep. 25, 2009

(87) PCT Pub. No.: WO2008/080035
PCT Pub. Date: Jul. 3, 2008

(65) Prior Publication Data
US 2013/0006383 A1    Jan. 3, 2013

Related U.S. Application Data

(60) Provisional application No. 60/876,854, filed on Dec. 21, 2006.

(51) Int. Cl.
*A61F 2/02*    (2006.01)

(52) U.S. Cl.
USPC .................................................. 623/23.72

(58) Field of Classification Search
CPC ............ A61L 2400/12; A61L 2430/32; A61L 27/227; A61L 27/54; A61L 2300/414; A61L 27/58; A61L 27/26; A61L 2430/38; A61L 31/146; A61L 31/148; A61L 15/44; A61L 2300/412; A61L 2300/608; B82Y 30/00; B82Y 5/00; C12N 2533/30; B01D 2239/025; B01D 2239/0631; B01D 2239/064; B01D 2239/0681; B01D 46/546; B29C 65/488; B29C 47/0014; B29C 66/435; A61K 2300/00; A61K 38/10; A61K 38/18; A61K 9/70; A61K 35/30; A61K 38/1825; D01D 5/003; D01D 5/0084; D01D 5/0007; D01D 5/38; B01J 20/28007; B01J 20/3242; B01J 20/28038; A61F 2002/3084; D01F 1/10; D01F 11/14; D01F 6/14; D01F 6/22; D01F 11/12; D01F 11/16; D01F 1/02; D01F 4/00; D01F 6/52; D01F 6/60; D01F 6/66; D01F 6/82; D01F 8/00; D01F 9/08; D01F 9/14
USPC .......... 424/400, 484, 423, 443; 977/762, 773, 977/906, 923, 770, 902; 435/398; 514/7.6, 514/1.1, 9.1; 428/113, 114, 293.7, 373, 428/375, 378, 392; 530/300, 402; 623/23.72
See application file for complete search history.

(56) References Cited

U.S. PATENT DOCUMENTS

| | | | |
|---|---|---|---|
| 6,743,273 B2 | 6/2004 | Chung et al. | 55/482 |
| 2005/0038498 A1 | 2/2005 | Dubrow et al. | 623/1.15 |
| 2005/0095695 A1 | 5/2005 | Shindler et al. | 435/285.1 |
| 2007/0082393 A1 | 4/2007 | Lodhi et al. | 435/325 |

OTHER PUBLICATIONS

Rochkind et al. Development of a tissue-engineered composite implant for treating traumatic paraplegia in rats. Eur Spine J. Feb. 2006; 15(2): 234-245. Published online Nov. 15, 2005.*
Ahmed et al., "Three-dimensional nanofibrillar surfaces covalently modified with tenascin-C-derived peptides enhance neuronal growth in vitro", J Biomed Mater Res 2006 76A:851-860.
Gill et al., "Expresion of a dominant negative FGF receptor in development GNRH1 neurons disrupts axon outgrowth and targeting to the median eminence", Biology of Reproduction 2006 74:463-472.
Li et al., "Electrospun nanofibrous structure:A novel scaffold for tissue engineering", J Biomed Mater Res 2002 60:613-621.
Rabchevsky et al., "Basic fibroblast growth factor (bFGF) enhances functional recovery following severe spinal cord injury to the rat", Experimental Neurology 2000 164:280-291.
Recknor et al., "Directed growth and selective differentiation of neural progenitor cells on micropatterned polymer substrates", Biomaterials 2006 27:4098-4108.
Schindler et al., "A synthetic nanofibrillar matrix promotes in vivo-like organization and morphogenesis for cells in culture", Biomaterials 2005 26:5624-5631.
Teng et al., "Basic fibroblast growth factor increases long-term survival of spinal motor neurons and improves respiratory function after experimental spinal cord injury", The Journal of Neuroscience 1999 19(16):7037-7047.
Webber et al., "Multiple signaling pathways regulate FGF-2-induced retinal ganglion cell neurite extension and growth cone guidance", Mol. Cell. Neurosci. 2005 30:37-47.
Yang et al., "Electrospinning of nano/micro scale poly($_L$lactic acid) aligned fibers and their potential in neural tissue engineering", Biomaterials 2005 26:2603-2610.

* cited by examiner

*Primary Examiner* — Gregory S Emch
(74) *Attorney, Agent, or Firm* — Licata & Tyrrell P.C.

(57) ABSTRACT

The invention relates to a device composed of a plurality of strips of randomly oriented nanofibers, wherein said strips are arranged along their longitudinal axes. In addition, the surface of the device's nanofibers are covalently modified with fibroblast growth factor-2. A method for using the instant device for facilitating axonal regeneration in spinal cord injury is also provided.

2 Claims, 2 Drawing Sheets

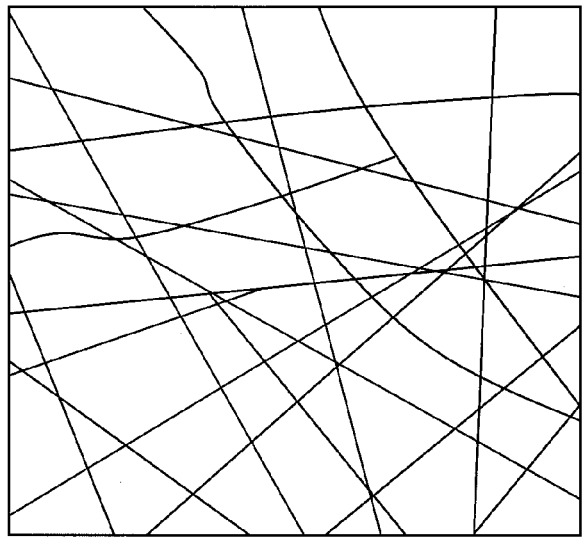
FIG. 1
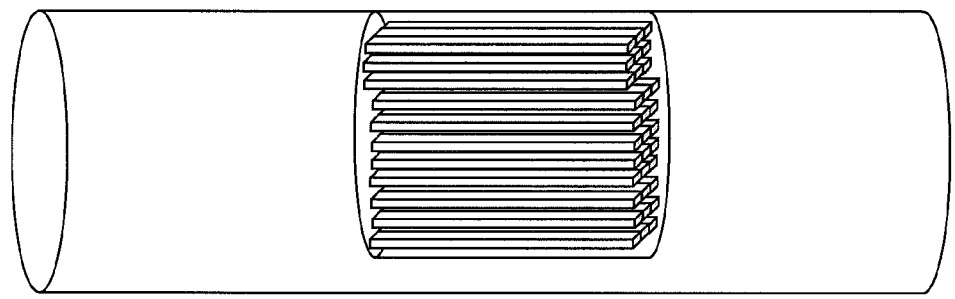
FIG. 2A
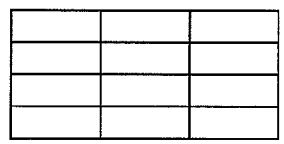          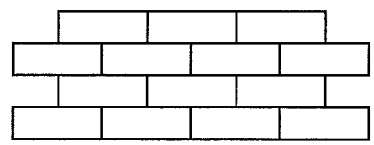
FIG. 2B                FIG. 2C

RANDOMLY ORIENTED, FGF-2-MODIFIED NANOFIBER DEVICE FOR USE IN SPINAL CORD REPAIR This patent application is the National Stage of International Application No. PCT/US2007/088493 filed Dec. 21, 2007, which claims the benefit of priority from U.S. Provisional Patent Application Ser. No. 60/876,854, filed Dec. 21, 2006, teachings of each of which are herein incorporated by reference in their entirety.

BACKGROUND OF THE INVENTION

During development of and following injury to the nervous system, the growth and regeneration of axons is strongly influenced by astrocyte-derived extracellular matrix molecules (Silver & Miller (2004) *Nat. Rev. Neurosci.* 5:146-156) and Schwann cell-derived basement membrane molecules (Chernousov & Carey (2000) *Histol. Histopathol.* 15:593-601). The basement membrane is a structurally compact form of the extracellular matrix. Examples of such molecules include thrombospondin in the extracellular matrix (Adams & Tucker (2000) *Dev. Dyn.* 218:280-299) and laminin-1 in the basement membrane (Chernousov & Carey (2000) supra). In this regard, the extracellular matrix produced by astrocytes includes both positive (e.g., thrombospondin, fibronectin) and negative (e.g., chondroitin and keratan sulphate proteoglycans) effectors of neuronal growth (Lein (1992) *Brain Res. Dev. Brain Res.* 69:191-197; Kearns, et al. (2003) *Exp. Neurol.* 182:240-244; Silver (1994) *J. Neurol.* 242:S22-4; Silver & Miller (2004) supra).

Electrospun nanofibers have been suggested as providing a scaffold that mimics the extracellular matrix (Li, et al. (2002) *J. Biomed. Mater. Res. A* 60:613-621). Nanofibers produced via the process of electrospinning have unprecedented porosity, a high surface to volume ratio, and high interconnectivity, all physical properties that are ideal for cellular attachment and growth (Li, et al. (2002) supra). The nanofiber aggregates can be deposited in either a random or aligned array, to result in random or oriented axonal growth (Yang, et al. (2005) *Biomaterial* 26:2603-2610). Nanofibers electrospun from a variety of synthetic and naturally occurring polymers have generated tremendous interest due to their potential as scaffolds for regenerating tissue (Kidoaki, et al. (2005) *Biomater.* 26:37-46; Ma, et al. (2005) *Tissue Eng.* 11:1149-1158; Venugopal & Ramakrishna (2005) *Appl. Biochem. Biotechnol.* 125:147-158; Schindler, et al. (2006) *Cell Biochem. Biophys.* 45:215-228), with a recent study indicating that silk nanofibers improved bone regeneration in the rabbit (Kim, et al. (2005) *J. Biotechnol.* 120:327-339).

Tenascin-C, a multi-domain, multi-functional extracellular matrix glycoprotein with neuro-regulatory actions (Gotz, et al. (1996) *J. Cell Biol.* 132:681-699; Dorries, et al. (1996) *J. Neurosci. Res.* 43:420-438; Meiners & Geller (1997) *Mol. Cell Neurosci.* 10:100-116; Meiners & Mercado (2003) *Molec. Neurobiol.* 27:177-196; Meiners, et al. (2001) *J. Neurosci.* 21:7215-7225) has also been shown to provide a chemical cue that might enhance the function of a nanofibrillar scaffold. Research has also focused on the growth-promoting actions of the alternatively spliced fibronectin type III region of human tenascin-C. The active site for neurite outgrowth in this region was localized from cerebellar granule, cerebral cortical, spinal cord motor, and dorsal root ganglion neurons to a peptide with amino acid sequence Val-Phe-Asp-Asn-Phe-Val-Leu-Lys-Ile-Arg-Asp-Thr-Lys-Lys (SEQ ID NO: 1) (Meiners, et al. (2001) supra; Ahmed, et al. (2006) *J. Biomed Mater. Res. A* 76:851-860), called the D5 peptide. It was recently demonstrated that covalent modification of electrospun polyamide nanofibers with the D5 peptide promoted more in vivo-like growth patterns for neurons, with long, well elaborated processes (Ahmed, et al. (2006) supra).

Moreover, chitosan nanofibers modified with bone morphogenetic protein-2 enhanced adhesion and proliferation of and calcium deposition by osteoblastic cells; the effect on adhesion was dose-dependant with the amount of bone morphogenetic protein-2 attached to the nanofiber surface (Park, et al. (2006) *Biotehnol. Appl. Biochem.* 43:17-24). Furthermore, derivatization of poly(caprolactone) nanofibers with gelatin increased endothelial cell proliferation and allowed the cells to maintain their expression of platelet-endothelial cell adhesion molecule 1, intercellular adhesion molecule 1, and vascular cell adhesion molecule 1 in culture (Ma, et al. (2005) supra).

SUMMARY OF THE INVENTION

The present invention is a device composed of a plurality of strips of randomly oriented nanofibers, wherein said strips are arranged along their longitudinal axes and the surface of the nanofibers are covalently modified with fibroblast growth factor-2. A method for using the instant device to facilitate axonal regeneration following spinal cord injury is also provided.

BRIEF DESCRIPTION OF THE DRAWINGS

FIG. 1 illustrates a fibrous network of randomly oriented nanofibers with pores interspersed therein.

FIG. 2 illustrates a plurality of strips of randomly oriented nanofibers, wherein said strips are arranged along their longitudinal axes. FIG. 2A depicts stacked strips of nanofibers implanted into an injured spinal cord. FIGS. 2B and 2C show a cross section of bundles strips of nanofibers which have been stacked on top of each other (FIG. 2B) or staggered (FIG. 2C).

DETAILED DESCRIPTION OF THE INVENTION

Figure 3:
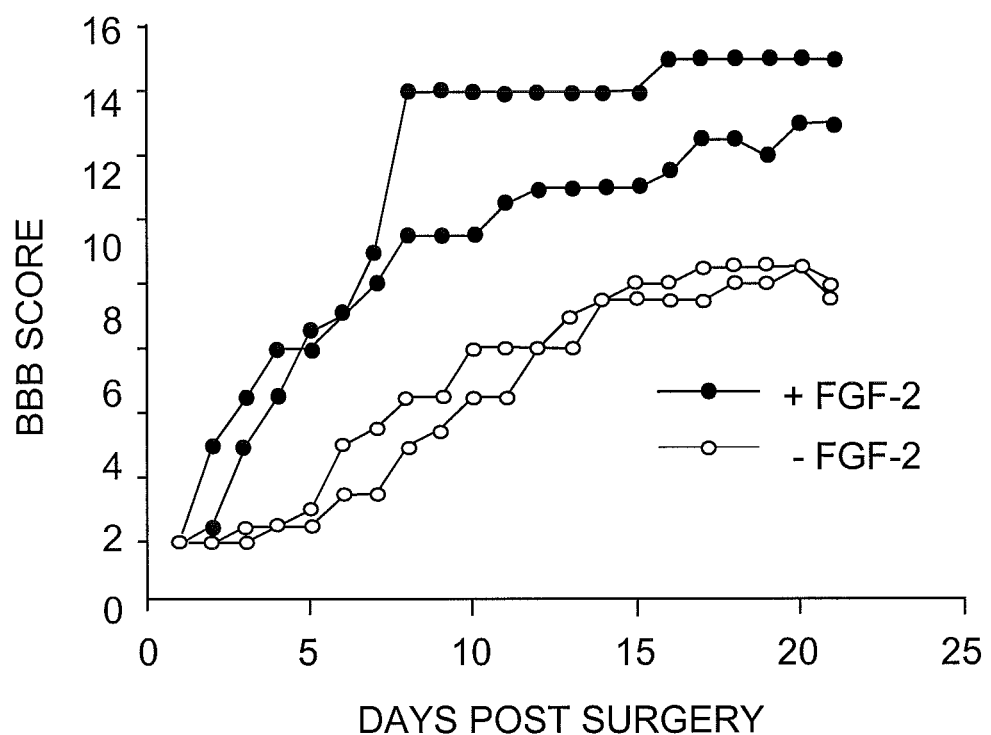
FIG. 3 shows the hindlimb functional assessment with the Basso, Beattie, Bresnahan (BBB) locomotor rating scale. Each curve is from one individual animal. Animals were tested daily for 3 weeks. Rats that received an FGF-2-modified nanofiber device (closed circles) showed enhanced functional recovery in comparison to rats that received an unmodified nanofiber device (open circles).

Axons of the spinal cord follow a strict topography, much of which needs to be recreated in order to permit reconnection of appropriate circuits and maximal functional recovery following injury. Structures employed in support of the regeneration process must incorporate within their design the ability to be "stealthy" and not elicit the foreign body response or recognition by the immune system. Moreover, both chemistry and geometry of the extracellular matrix are critical for proper neuronal function, necessitating that an optimized biomimetic surface for central nervous system (CNS) repair incorporate both types of cues. Because neurites extend along the axis of nanofibers, nanofibers with a parallel orientation would appear to be ideal for encouraging targeted axonal regeneration in the damaged spinal cord. However, aligned nanofibers exhibit considerable rigidity in comparison to randomly oriented nanofibers, and thus implants of aligned nanofibers may cause further damage to the delicate spinal cord tissue. It has now been found that a spinal cord prosthetic device that incorporates narrow strips of randomly oriented nanofibers that are longitudinally bundled, provides appropriate geometric cues for axonal regrowth. The analysis disclosed herein indicates that such a device can correctly guide regenerating axons across the injury gap created by an over-hemisection to the adult rat thoracic spinal cord. In addition, devices that incorporate nanofibers modified with fibroblast growth factor-2 (FGF-2) encourage substantially more axonal regeneration and better functional recovery (assessed using the Basso, Beattie, Bresnahan (BBB) locomotor rating scale) than do devices that incorporate unmodified nanofibers. Furthermore, an FGF-2-modified device also encourages revascularization. Neither type of device promote glial scarring or induced an apparent foreign body or inflammatory response.

Accordingly, the present invention is device or construct composed of a plurality of strips of randomly oriented nanofibers, wherein said strips are arranged along their longitudinal axes and the surface of the nanofibers are covalently modified with FGF-2. Given that such devices greatly enhance the promotion of neurite outgrowth, the instant devices find application as scaffolds for the regrowth of damaged spinal cord axons and support for spinal cord repair.

The term "nanofiber" as used herein means a polymer fine fiber of a diameter of about 1000 nanometers or less composed of a non-cytotoxic polymer. In particular embodiments, the nanofiber is 5 to 1000 nanometers. The polymer can be water soluble or water insoluble. The polymer can be biodegradable and/or biodissolvable. In certain embodiments, the polymer is a polyester or polyamide. For example, a polyester can be an aliphatic polyester including, but not limited to polylactide, poly(glycolate), poly($\epsilon$-caprolactone), and copolymers thereof. In particular embodiments, the polymer is a polyamide. Polyamides include, but are not limited to, polycaprolactam, nylon 6, a nylon 66, nylon 6 12 or other nylon blend. As is conventional in the art, nylon is a generic name for all long chain synthetic polyamides. Typically, nylon nomenclature includes a series of numbers such as in nylon-6,6 which indicates that the starting materials are a $C_6$ diamine and a $C_6$ diacid (the first digit indicating a $C_6$ diamine and the second digit indicating a $C_6$ dicarboxylic acid compound). Another nylon can be made by the polycondensation of epsilon caprolactam in the presence of a small amount of water. This reaction forms a nylon-6 (made from a cyclic lactam, also known as epsilon-aminocaproic acid) that is a linear polyamide. Further, nylon copolymers are also contemplated. Copolymers can be made by combining various diamine compounds, various diacid compounds and various cyclic lactam structures in a reaction mixture and then forming the nylon with randomly positioned monomeric materials in a polyamide structure. For example, a nylon 6,6-6,10 material is a nylon manufactured from hexamethylene diamine and a $C_6$ and a $C_{10}$ blend of diacids. A nylon 6-6,6-6,10 is a nylon manufactured by copolymerization of epsilon aminocaproic acid, hexamethylene diamine and a blend of a $C_6$ and a $C_{10}$ diacid material.

Advantageously, cultured neurons adhere to polyamide nanofibers more readily than to nanofibers composed of other polymers. Furthermore, nanofibers composed of polyamide produce no apparent neurotoxicity and do not rapidly degrade, maintaining their structural integrity in vivo for several weeks. Indeed, it seems likely that the formation and maintenance of the reformed neuronal circuitry within the spine might be best facilitated and maintained by a prosthetic device that only degrades slowly within the body.

Moreover, breakdown of rapidly biodegradable materials such as polyglycolate or polylactate can result in the release of monomers (e.g., lactate) that have been shown to significantly lower the local pH 4, with probable adverse effects for the regenerating axons. In addition, thin layers of polyamide nonwoven fabrics are flexible (Moeschel, et al. (2002) *Biotech. Bioeng.* 82:190-199). This property is maintained and exceeded in the instant device composed of longitudinally bundled strips of polyamide nanofibrillar fabric, allowing for excellent incorporation into the damaged spinal cord.

The nanofibers of the instant device are said to be randomly oriented in that they are randomly distributed in space, i.e., they are not oriented in a parallel manner (see FIG. 1). In this regard, the nanofibers form an interconnecting net (e.g., a sheet or fabric in one plane) with spacing between fibers selected to promote growth and culture stability. Such spacing forms pores or channels with a diameter of about 0.01 microns to about 25 microns or desirably about 2 microns to about 10 microns, through a thickness.

The instant nanofibers can be prepared by electrospinning techniques routinely performed in the art. See, e.g., U.S. Pat. No. 6,743,273. Electrospinning is a physical process that can produce nanofiber aggregates having unprecedented porosity, high interconnectivity, and fiber surfaces with a high surface to volume ratio, all physical properties that are ideal for cell attachment and growth (Li, et al. (2002) *J. Biomed. Mater. Res. A* 60:613-621). Advantageously, the geometry of electrospun nanofibers mimics the fibrillar organization of the extracellular matrix that forms a network for neuronal attachment and axonal growth during central nervous system development. As is conventional in the art, the nanofibers are electrospun into a layer, also generally referred to as fabric. A layer of electrospun nanofibers can be 0.5 micron to 5 micron thick, or more desirably about 2 micron thick.

As disclosed herein, a layer of randomly oriented nanofibers which have been cut into strips, wherein the strips have been arranged next to and on top of one another along their longitudinal axes, provides appropriate geometric cues for axonal regrowth. Because of the arrangement of the nanofibers in strips, the instant device is more flexible then conventional nanofiber structures, i.e., more flexible than nanofibers arranged parallel to one another and more flexible than continuous sheets of randomly oriented nanofibers. Accordingly, the instant invention provides for a plurality of strips of nanofibers arranged along their longitudinal axes. As used herein, a plurality of strips is intended to mean two or more strips, wherein the number of strips employed is dependent upon and the size of the injury being treated. Strips of randomly oriented nanofibers can be cut to a width of 0.1 mm to 1 mm, 0.25 mm to 0.75 mm, or more desirably 0.5 mm to allow ample room or axonal fasciculation. It is contemplated that the length of the strips can range from 0.1 mm to 5 mm and can be cut to the size of the injury being treated (FIG. 2A). The strips are arranged along their longitudinal axes (FIG. 2A) and can be stacked directly on top of each other (FIG. 2B) or staggered (FIG. 2C). In this regard, multiple layers of discontinuous nanofibers are produced to bridge injuries in a damaged spinal cord.

In some embodiments, the strips are separated by a spacer. The term "spacer", as used herein, means a layer separating the strips of nanofibers such that the strips are separated by the diameter or thickness of the spacer. Desirably the spacer has a thickness of about 10 microns to about 50 microns. However, the invention also encompasses nanofibrillar layers that are separated by 50 to 100 µm to allow more room for cellular growth. The spacer can be water soluble or water insoluble. The spacer can be porous or nonporous. Porosity of the spacer is determined by cellular penetration. A cell is able to penetrate a porous spacer but is not able to penetrate a non-porous spacer. The spacer can be biodegradable and/or biodissolvable. Desirably, the spacer is biocompatible. The spacer can be a polymer including cellulose, starch, or other polysaccharide such as agarose.

The results presented herein indicate that nanofibers alone are not sufficient to promote optimal axonal regeneration and functional recovery following spinal cord injury. The chemistry as well as geometry of the extracellular matrix is critical for proper neuronal function. FGF-2, a multi-functional growth factor, has been shown to be involved in promoting cell survival, stimulating neurite outgrowth, guiding extending neuronal processes (Webber, et al. (2005) *Mol. Cell Neurosci.* (30:37-47; Gill & Tsai (2006) *Biol. Repro.* 74:463-472), and with actions on both motor and sensory neurons (Ten, et al. (1999) *J. Neurosci.* 19:7037-7047; Rabchevsky, et al. (2000) *Exp. Neurol.* 164:280-291). FGF-2, when expressed by adenoviral injection within glia in the dorsal spinal cord, results in regeneration of crushed axons within the dorsal root and significant recovery of thermal sensory function (Rabchevsky, et al. (2000) supra). Furthermore, continuous intrathecal administration of soluble FGF-2 to the spinal cord following contusion injury significantly improves recovery of hindlimb function (Romero, et al. (2001) *J. Neurosci.* 21:8408-8416). Indeed, strips of longitudinally bundled nanofibers covalently modified with FGF-2 can increase axonal regeneration in the over-hemisected rat thoracic spinal cord and improve hindlimb functional recovery (FIG. 3). The advantage of such a device is manifest in cases involving large injuries with extensive tissue loss.

It has been found that a significant practical advantage of using immobilized FGF-2 is that the growth factor is far more potent when immobilized on nanofibers than when presented to cells as a soluble molecule. In addition, FGF-2-modified nanofibers can be stored in their dry state for 6 months at 4° C. with retention of significant biological activity. In contrast, soluble FGF-2 is notoriously unstable, with an approximate half-life in tissue culture media of 6-8 hours (Caldwell, et al. (2004) *Exp. Neurol.* 188:408-420). The stability of bound FGF-2 is an attribute that facilitates the production of prefabricated spinal cord prosthetic devices in bulk, trimmed to fit into a variety of defects, and ready for use as the need arises. In addition, it is contemplated that FGF-2-modified devices can be used in the repair of damage within the peripheral nervous system (PNS).

Accordingly, particular embodiments of the present invention embrace the covalent modification of the nanofibers with FGF-2. FGF-2 used in accordance with the present invention can be isolated from a natural source of recombinantly produced according to conventional methods.

The amino acid sequence of FGF-2 is well-known in the art and mammalian FGF-2 proteins are available under GENBANK Accession Nos. NP_001997 (*Homo sapiens*), NP_032032 (*Mus musculus*), NP_062178 (*Rattus norvegicus*) and NP_990764 (*Gallus gallus*). Moreover, recombinant mammalian FGF-2 proteins are readily available from commercial sources such as Peprotech, Inc. (Rocky Hill, N.J.).

FGF-2 protein can be covalently attached to the nanofibers using any suitable chemistry. In some embodiments, functional groups are incorporated at the outside surface of the nanofibers. In this regard, the functional groups can be reacted to bind FGF-2 as well as other peptides, polypeptides, lipids, carbohydrates, polysaccharides, amino acids, nucleotides, nucleic acids, polynucleotides, or bioactive molecules to the surface of the nanofiber. Functional groups can be deposited on the surface of a nanofiber by plasma deposition. Plasma deposition creates local plasmas at the surface of the nanofiber. The treated surface is then reacted with gaseous molecules, such as allylamine and/or allyl alcohol, in a reaction chamber. In another embodiment, functional groups are introduced onto the surface of the nanofibers during the electrospinning process. Dodecyl amine, dodecyl aldehyde, dodecyl thiol, or dodecyl alcohol can be added to the polymer solution. The polymer solution is than electrospun into nanofibers in which a portion of the added amines, aldehydes, sulphydryl, or alcohol moieties, respectively, are exposed on the outside surface of the nanofibers.

As indicated, in addition to FGF-2, other bioactive molecules can be incorporated or covalently attached to the nanofibers. Likewise, bioactive molecules can be incorporated into the spacer. Bioactive molecules of particular interest include human or veterinary therapeutics, nutraceuticals, vitamins, salts, electrolytes, amino acids, peptides, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, neurotransmitters, pheromones, chalones, prostaglandins, immunoglobulins, monokines and other cytokines, humectants, minerals, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules. Glycoaminoglycans include glycoproteins, proteoglycans, and hyaluronan. Polysaccharides include cellulose, starch, alginic acid, chytosan, or hyaluronan. Cytokines include, but are not limited to, cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5, interleukin (IL) 1, IL-2, IL-3, IL-4, IL-5, IL-6, IL-7, IL-8, IL-9, IL-10, IL-11, IL-12, IL-13, TNF-alpha, and TNF-beta. Immunoglobulins useful in the present invention include, but are not limited to, IgG, IgA, IgM, IgD, IgE, and mixtures thereof. Amino acids, peptides, polypeptides, and proteins may include any type of such molecules of any size and complexity as well as combinations of such molecules. Examples include, but are not limited to, structural proteins, enzymes, and peptide hormones.

Bioactive molecule can also include fibrous proteins, adhesion proteins, adhesive compounds, deadhesive compounds, and targeting compounds. Fibrous proteins include collagen and elastin. Adhesion/deadhesion compounds include fibronectin, laminin, thrombospondin and tenascin C. Adhesive proteins include actin, fibrin, fibrinogen, fibronectin, vitronectin, laminin, cadherins, selectins, intracellular adhesion molecules 1, 2, and 3, and cell-matrix adhesion receptors including but not limited to integrins.

The term bioactive molecule also includes leptin, leukemia inhibitory factor (LIF), RGD peptide, tumor necrosis factor alpha and beta, endostatin, angiostatin, thrombospondin, osteogenic protein-1, bone morphogenic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18.

Growth factor, as used herein, means a bioactive molecule that promotes the proliferation and/or differentiation of a cell or tissue. Growth factors useful in the present invention include, but are not limited to, transforming growth factor-alpha (TGF-alpha), transforming growth factor-beta (TGF-beta), platelet-derived growth factors (PDGF), fibroblast growth factors (FGF), nerve growth factors (NGF), brain derived neurotrophic factor, cartilage derived factor, bone growth factors (BGF), insulin-like growth factor (IGF), vascular endothelial growth factor (VEGF), granulocyte colony stimulating factor (G-CSF), hepatocyte growth factor, glial neurotrophic growth factor (GDNF), stem cell factor (SCF), keratinocyte growth factor (KGF), skeletal growth factor, bone matrix derived growth factors, and bone derived growth factors and mixtures thereof.

The nanofiber device of the present invention can be used in many known applications employing nanofibers including, but not limited to, filter applications and pharmaceutical applications. In a further application, the nanofiber devices can be used in high throughput drug analysis and drug sensitivity analysis to provide an environment for the cells to more closely mimic the in vivo nature of the cells in an ex vivo environment thereby facilitating analysis of axonal regeneration in the presence of a test agent. More specifically, the nanofiber device is useful in a variety of biological applications, including cell culture, tissue culture, and tissue engineering applications. In this regard, a particular embodiment of the present invention provides a method for facilitating axonal regeneration following spinal cord injury by contacting an injured spinal cord with the nanofiber device of the invention thereby facilitating axonal regeneration and treatment of the spinal cord injury. In some embodiments, the nanofiber device is seeded with cells prior to being implanted into a spinal cord injury. Such cells can include undifferentiated or differentiated neurons or stem cells. Conventional microscopic methods or behavioral analysis can be employed to determine whether the nanofiber device has achieved axonal regeneration in the subject with a spinal cord injury.

The invention is described in greater detail by the following non-limiting examples.

EXAMPLE 1

Materials and Methods

Polyamide Nanofibers. Randomly oriented polyamide nanofibers (a continuous fiber that collects as a nonwoven fabric) were electrospun by Donaldson Co., Inc. (Minneapolis, Minn.). They were electrospun from a blend of two polymers [$(C_{28}O_4N_4H_{47})_n$ and $(C_{27}O_{4.4}N_4H_{50})_n$], either onto plastic coverslips for the imaging studies or as a free fabric for the spinal cord studies. The polymeric nanofiber mat was crosslinked in the presence of an acid catalyst and formed a network of filaments on average 180 nm in diameter interspersed with pores 100-800 nm in diameter (Schindler, et al. (2005) *Biomaterials* 26:5624-5631) (FIG. 1). In some cases the nanofibers were covalently coated with a proprietary polyamine polymer by Surmodics, Inc. (Eden Prairie, Minn.) so as to provide a functional group for further covalent modification of the nanofibers with bioactive peptides.

Nanofibers (unmodified) for the imaging studies were visualized using AFM as follows. Tapping mode AFM was performed in ambient air using a Nanoscope IIIa MulitMode system from Veeco Instruments, Inc (Woodbury, N.Y.). A J-scanner with a maximum 125×125 $\mu^2$ x-y scan range and etched silicon tips with a nominal 5-10 nm tip radius of curvature were used.

Nanofibers for spinal cord studies were either unmodified or covalently modified with FGF-2 or a neurite outgrowth promoting peptide derived from tenascin-C, called the D5' peptide (Ahmed et al. (2006) supra) The amino acid sequence of the D5' peptide is Ala-Asp-Glu-Gly-Val-Phe-Asp-Asn-Phe-Val-Leu-Lys-Ile-Arg-Asp-Thr-Lys-Lys-Gln (SEQ ID NO: 2), where Phe-Asp and Phe-Val are required for facilitation of neurite extension (Meiners et al. (2001) supra).

Analysis of individual nanofibers of FGF-2-modified electrospun polyamide fabric (~2 μm thick) revealed a median fiber diameter of approximately 180 nm, surface smoothness to within 5 nm over a length of 1.5 microns, and a pore diameter of approximately 700 nm (Schindler, et al. (2005) *Biomaterials* 26:5624-5631).

Nanofiber Device. Nanofiber strips were cut to a width of 0.5 mm to allow ample room for axonal fasciculation and to a length of 2 mm. The strips were dipped one by one into SEAPREP® agarose and stacked next to and on top of each other to result in a device ~2 mm high and 3 mm wide when hydrated. This agarose has a gelling temperature of 8-17° C., and, without special preparation (e.g., cooling with liquid nitrogen) remains semi-liquid at room temperature. Thus, it provides a liquid or semi-liquid medium at body temperature to allow for ready infiltration of cells and fasciculation of axons in between nanofiber layers.

Surgical Procedure and Postoperative Care. To investigate whether polyamide nanofibers allow axonal regrowth in vivo following CNS injury, unmodified or peptide-modified nanofibers were incorporated into an over-hemisection spinal cord injury model. The subjects of this study included animals with unmodified nanofibrillar implants, animals with modified nanofibrillar implants, and injury only control animals for the visualization of axons (3 weeks survival time). Animals with unmodified nanofibrillar implants and injury only control animals were also used for the visualization of cell bodies (3 and 5 weeks survival time; 5 animals for each group and each time point).

Adult female Sprague Dawley rats (250-260 gm) were anesthetized using ketamine/xylazine (75 mg/kg+10 mg/kg, intramuscular (IM)). They were also given buprenorphine (0.05 mg/kg, delivered subcutaneously) on a pre-emptive basis for post-operative pain. A laminectomy was made at the thoracic level 8-9 ($T_{8-9}$) spinal vertebrae. Iridectomy scissors were stereotaxically positioned at the dorsal midline of the spine and lowered to a depth of 2.0 mm.

Another transverse cut was made 2 mm caudal to the first, and the tissue in between was removed with scissors. A nanofiber device (unmodified or modified with FGF-2) was carefully implanted into the lesion site. Control animals received no nanofibers. The musculature was sutured and the skin was closed with surgical clips. All animal procedures were performed in strict accordance with institutional guidelines.

Animals were allowed to recover in clean cages atop heating pads. They were observed for infection or lethargy and were treated for 4 or more days post-surgery with buprenorphine analgesic (0.05 mg/kg, 2-3 times daily, delivered subcutaneously). Animals were also injected subcutaneously with enrofloxacin (Baytril) antibiotic for 3 or more days to manage bladder infections (5 mg/kg, 2 times daily) and with Ringer's lactate solution (5 ml, 3 times daily, delivered subcutaneously) for 2-3 days (or until animals were observed to be drinking on their own) to manage dehydration (15 ml daily). Bladders were evacuated 3 times daily until autonomic bladder function was restored (usually 4-7 days).

Immunohistochemistry. Following postoperative periods of 3 or 5 weeks, animals were transcardially perfused under deep terminal anesthesia (sodium pentobarbital, 100 mg/kg, intraperitoneal (IP)) with 4% paraformaldehyde in 0.1 M sodium phosphate buffer. Spinal cords were removed and sagitally sectioned on a cryostat at 20 μm. Sections were mounted on poly-L-lysine-coated glass slides and stained for cell bodies using Nissl stain or immunolabeled for axons using monoclonal mouse antibody against neurofilament-M (Chemicon, Temecula, Calif.) (1:400 dilution overnight at room temperature) followed by a CY3-conjugated goat anti-mouse secondary antibody (Jackson ImmunoResearch, West Grove, Pa.) (1:500 dilution for 1 hour at room temperature). Slides were examined using a ZEISS AXIOPLAN microscope equipped with an epi-fluorescence illuminator.

EXAMPLE 2

Biocompatibility of Nanofibers

The nanofibers were slowly degradable, with non-cytotoxic degradation products, and the nanofibers maintained their structural integrity in vivo for several weeks. It was rationalized that the formation and then maintenance of the reformed neuronal circuitry within the spine might be best facilitated and maintained by scaffolds that only slowly degrade within the body. Moreover, breakdown of rapidly biodegradable materials such as polyglycolate or polylactate can result in the release of monomers (e.g., lactate) that can in turn significantly lower the local pH (Cordwener, et al. (2000) *Biomater.* 21:2433-2442) and negatively impact the viability of regenerating neurons. In addition, the utility of non- or slowly degrading materials in general, and polyamide in particular, in the promotion of axonal regrowth in the peripheral nervous system (PNS) has been shown (Yannas & Hill (2004) *Biomater.* 25:1593-1600). Moreover, thin layers of polyamide non-woven fabrics are extremely flexible (Moeschel, et al. (2002) supra), allowing for excellent incorporation into the damaged spinal cord.

To evaluate the biocompatibility of polyamide nanofibers and their potential as a regenerative matrix in the injured spinal cord, the following experiment was performed. Over-hemisections of the dorsal columns and the underlying corticospinal tract were performed at thoracic level 8 of the adult rat spinal cord as described herein, and a piece of nanofibrillar fabric (~2-4 µm thick, ~5×5 mm$^2$ square) composed of randomly oriented nanofibers was gently crumpled with a pair of micro-forceps and implanted into the wound. Atomic force microscopy (AFM) images of the nanofibrillar fabric electrospun onto plastic coverslips were evaluated and revealed a fibrous network of filaments interspersed with pores. The 2-4 µm thickness of the fabric was chosen because thinner layers of nanofibers are very difficult to handle, and heavier layers of nanofibers lose their flexibility and actually caused further damage to the spinal cord upon implantation. The fabric was well integrated into the host tissue 3 and 5 weeks after injury, with no evidence of cavitation. The implant of randomly deposited nanofibers demonstrated good host-graft integration 5 weeks after injury with no cavitation, whereas a large cavity was present in injury-only, control animals. Imaging of sequential sections showed that the lesion site was completely filled with nanofibers.

Axons were visualized 3 weeks after injury utilizing an antibody against neurofilament-M using epi-fluorescent microscopy. No axons were seen in the injury site in control animals (injury only, no nanofibers), whereas they extended onto the nanofibrillar fabric, detectable in the injury site as a consequence of its low level of autofluorescence. No labeling was detected when animals were sacrificed immediately after implantation of nanofibers, indicating that the observed axons represented regrowth, as opposed to axons spared in the lesion process.

Covalent modification of the nanofibers with an extended version of the D5 peptide, called the D5' peptide (SEQ ID NO: 2), which has 4 additional amino acids at its N-terminus to allow for better presentation of the Phe-Asp/Phe-Val active site to neurons, greatly increased their ability to facilitate neuronal process extension in vitro (Ahmed, et al. (2006) supra) and in vivo. Neurofilament M-labeled axons were observed within the implant of unmodified nanofibers and axonal growth was more robust within the implant of nanofibers modified with the D5' peptide. Axons were observed on the surface of the nanofibers following folds in the nanofibrillar fabric (i.e., axons grew more or less parallel to the axis of the spinal cord).

EXAMPLE 3

Tubular Device

While encouraging, experiments carried out with crumpled fabric were unsatisfactory because the fabric itself was randomly folded during implantation, and regenerating axons appeared to follow along with the surface contours of the random folds, with forward motion at times restricted. On the other hand, when the folds in the nanofibrillar fabric by chance fell parallel to the spinal cord axis, axons also grew with a parallel organization. Therefore, a multi-layered tubular device was generated, reminiscent of the bilayered tubular device fabricated by Kidoaki, et al. ((2005) *Biomaterials* 26(1):37-46) as a prototype scaffold for implantation into arteries. In this example, each layer (~1-2 µm thick) was separated by about 5-10 µm from the next.

For experimental testing, the tubular device is implanted into a completely transected or near-completely transected spinal cord instead of the more modest over-hemisected spinal cord used in previous studies, since very little sparing in the lateral corticospinal tract can lead to large effects on spared locomotion (Keyvan-Fouladi, et al. (2003) *J. Neurosci.* 23:9428-9434). This can in turn lead to difficulty in behavioral testing to assess the effectiveness of the implant in promoting functional recovery. Nanofibers to be used in human medicine are layers of nanofibers cut and stacked to fit the size of the injury following, if necessary, trimming away of the scar tissue, which impedes axonal elongation. In the experimental model, the diameter of the multi-layered tube is fashioned to match the diameter of the transected spinal cord with the orientation of the layers parallel to the spinal cord axis, allowing for longitudinally oriented axon growth. However, since neurite extension on randomly deposited nanofibers is itself random (Yang, et al. (2005) supra; Ahmed, et al. (2006) supra) this design is not likely to limit lateral or dorsal-ventral axonal growth.

EXAMPLE 4

Stacked Layers of Strips of Nanofibers

Axonal growth on the instant device, composed of a plurality of strips of randomly oriented nanofibers, was also analyzed in the lesioned spinal cord. The results of this analysis indicated that many more fasciculated neurofilament-M labeled axons were observed 3 weeks after injury on the surface of nanofiber strips covalently modified with FGF-2 in comparison to strips of unmodified nanofibers. The axons grew with the correct longitudinal orientation within the SCP, while agarose alone provided no guidance. Moreover, FGF-2-modified devices encouraged enhanced functional recovery in comparison to unmodified devices (FIG. 3).

EXAMPLE 5

Inflammation and Scarring Following Spinal Cord Injury

The inflammation and scarring response of spinal cord tissue to nanofibers was evaluated. Implantation of randomly folded, unmodified polyamide nanofibers resulted in no cavitation 3 and 5 weeks following injury and no up regulation of glial fibrillary acid protein (GFAP), a marker for reactive astrocytes. Moreover, little or no staining for chondroitin sulfate proteoglycans (CSPGs) was observed, a group of scar-associated molecules largely believed to be inhibitory to axonal regrowth (Tang, et al. (2003) *J. Neurosci. Res.* 71:427-444; McKeon, et al. (1991) *J. Neurosci.* 11:3398-3411). Fewer inflammatory cells were also noted two weeks following injury.

Similar results were obtained when a plurality of strips of randomly oriented nanofibers covalently modified with FGF-2 were employed. Implantation of unmodified or FGF-2-modified nanofiber strips failed to promote up regulation of GFAP or to induce cavitation. In addition, revascularization (detected by fibronectin immunolabeling) was observed with within FGF-2-modified devices. While the fibronectin antibody only cross-reacted with a few blood vessels, collagen IV immunolabeling revealed that the implant contained an abundance of blood vessels. Many biomaterials provoke a considerable foreign body response, with heightened inflammation and encapsulation of the implant by scar tissue (Anderson & Shive (1997) *Adv. Drug Deliv. Rev.* 28:5-24). Therefore, the results presented herein indicate that the instant nanofiber device will be efficacious in the treatment of spinal cord injury. Not wishing to be bound by theory, it is believed that nanofibers attenuate scarring because of the nanofibrillar chemistry and/or the nanofibrillar nanostructure and porosity, which closely resemble features of naturally occurring extracellular matrix/basement membrane scaffolds, look like "self".

What is claimed is:

1. A device comprising a plurality of strips of randomly oriented nanofibers, wherein said strips are arranged along their longitudinal axes and the surface of the nanofibers are covalently modified with fibroblast growth factor-2, and wherein said device facilitates axonal regeneration following spinal cord injury.

2. A method for facilitating axonal regeneration following spinal cord injury comprising contacting an injured spinal cord with the device of claim 1 thereby facilitating axonal regeneration of the injured spinal cord.

* * * * *